United States Patent [19]

Tibes et al.

[11] Patent Number: 4,668,684

[45] Date of Patent: May 26, 1987

[54] COMBINATION OF FLUPIRTIN AND ANTICHOLINERGIC ACTING SPASMOLYTIC

[75] Inventors: Ulrich Tibes, Frankfurt am Main; Carl H. Weischer, Bonn; Helmut Hettche, Offenbach am Main; Hans-Peter Breuel, Mainz; Dietmar Gunesch, Offenbach am Main, all of Fed. Rep. of Germany

[73] Assignee: Degussa Aktiengesellschaft, Frankfurt am Main, Fed. Rep. of Germany

[21] Appl. No.: 831,139

[22] Filed: Feb. 21, 1986

[30] Foreign Application Priority Data

Feb. 23, 1985 [DE] Fed. Rep. of Germany ....... 3506508
Mar. 22, 1985 [DE] Fed. Rep. of Germany ....... 3510248

[51] Int. Cl.[4] .................... A61K 31/36; A61K 31/435
[52] U.S. Cl. ..................................... 514/277; 514/466
[58] Field of Search ........................................ 514/277

[56] References Cited

PUBLICATIONS

Chem. Abst. 95(1981)-187018p.

*Primary Examiner*—Stanley J. Friedman
*Attorney, Agent, or Firm*—Cushman, Darby & Cushman

[57] ABSTRACT

A synergistic effect is noted when Flupirtin is combined with an anticholinergic spasmolytic.

12 Claims, No Drawings

COMBINATION OF FLUPIRTIN AND ANTICHOLINERGIC ACTING SPASMOLYTIC

BACKGROUND OF THE INVENTION

Flupirtin is a medicine having analgetic properties. Its chemical name is 2-amino-3-carbethoxyamino-6-(4-fluoro-benzylamino)-pyridine and it has the following structural formula

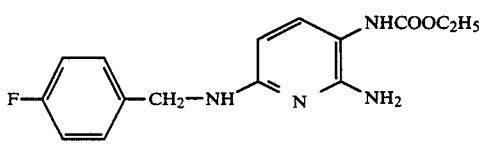

Flupirtin and its salts with physiologically unobjectionable acids has as an outstanding analgetic primary effect.

SUMMARY OF THE INVENTION

It has now been found that the effect of Flupirtin and its salt can be unexpectedly increased by combination with spasmolytics while simultaneously the effect of the spasmolytics likes experiences an increase. The active materials of the combination of the invention thus potentiate each other in their action.

The invention is directed to the manufacture of improved medicines having analgetic and spasmolytic action.

Specifically the invention is directed to medicines containing as active material Flupirtin or a physiologically unobjectionable salt thereof and at least one anticholinergically acting spasmolytic which has an analgetic action. Preferred spasmolytics are butylscopolammonium salts, Fenpiverinium salts, Trospium salts, Pramiverin salts and Ciclonium salts and their derivatives.

The dosage unit for example can contain per part by weight of Flupirtin 0.05 to 150, preferably 0.1 to 100 parts by weight of the spasmolytic. Thus there can be used a combination of 10 to 900 mg of Flupirtin and 0.3 to 100 mg of the spasmolytic, more preferably 10 to 600 mg of Flupirtin and 0.3 to 100 mg of spasmolytic, or still more preferably 30 to 600 mg of Flupirtin and 3 to 60 mg of the spasmolytic butylscopolamine (as the cation), most preferably 30 to 400 mg of Flupirtin and 3 to 60 mg of the spasmolytic butylscopolamine (as the cation).

Similarly there can be used the combination of 10 to 900 mg of Flupirtin and 5 to 60 mg Ciclonium base (as the cation).

In the claims the amounts by weight or parts by weight refer to Flupirtin per se as a pure material (i.e. not to salts of the pure active material, although such salts can be used) while with the spasmolytic reference is always to the salts in each case based on the cations present or base (in the latter case e.g. with Pramiverin).

The spasmolytics which are used in combination with the Flupirtin are spasmolytics which have an outstanding spasmolytic main action and a lower analgetic side component. Hereby it is a matter of spasmolytics whose action depends on the fact that they are anticholinergic.

Such spasmolytics for example are butylscopolamine, Fenpiverinium, Trospium, Pramiverin, and Ciclonium salts as well as their derivatives.

The Flupirtin is preferably used as an acid addition salt, in which case there are especially used the salts with hydrochloric acid (e.g. the hydrochloride or hydrobromide) or organic acids (e.g. maleate or gluconate). The spasmolytics are generally used in the form of their halogen salts, such as e.g. the chloride or bromide, thus e.g.

butylscopolammonium bromide
Fenpiverinium bromide
Trospium chloride
Pramiverin hydrochloride
Ciclonium bromide The Flupirtin and the spasmolytics can be used in general in the form of their salts with organic or inorganic acids which are suitable for the formation of therapeutically usable salts (i.e. salts of physiologically acceptable acids). As such acids there can be mentioned for example:

hydrochloric acids, e.g. hydrochloric acid, hydrobromic acid and hydroiodic acid, sulfuric acid, acids of phosphorus, e.g. phosphoric acids or phosphorous acid, nitric acid, perchloric acid, organic mono, di or tricarboxylic acids of the aliphatic, alicyclic, aromatic or heterocyclic series as well as sulfonic acids. Examples are:

formic acid, acetic acid, propionic acid, succinic acid, glycolic acid, lactic acid, malic acid, tartaric acid, citric acid, ascorbic acid, maleic acid, fumaric acid, malonic acid, adipic acid, hydroxymaleic acid, or pyruvic acid, phenylacetic acid, benzoic acid, p-aminosalicyclic acid, embonic acid, methanesulfonic acid, ethanesulfonic acid, hydroxyethanesulfonic acid, ethylenesulfonic acid, halogenbenzenesulfonic acid, e.g. chlorobenzenesulfonic acid, toluenesulfonic acid, naphthalene sulfonic acid, sulfanilic acid, or gluconic acid.

The spasmolytics used in the invention contain a basic nitrogen atom which is present in quarternary form. Hydrogen atoms which are located on this basic nitrogen atom can also be replaced by one or two $C_1$–$C_6$ alkyl groups, e.g. methyl, ethyl, propyl, isopropyl, butyl, sec.-butyl, amyl or hexyl. Likewise the alkyl groups which are present on this basic nitrogen atom can be replaced by one or two other $C_1$–$C_6$-alkyl group. These types of compounds are designated as derivatives or groups of the spasmolytics of the invention. The alkyl groups can be branched or straight chain. Thus for example in the case of butylscopolammonium cations the methyl group and/or the butyl group on quaternary basic nitrogen atom can be replaced by another $C_1$–$C_6$ alkyl group (e.g. methyl, ethyl, propyl, isopropyl, pentyl, hexyl). Likewise the methyl group on the basic nitrogen atom of the Fenpiverinium cation can be replaced by another $C_1$–$C_6$ alkyl group. The analogy is true, e.g. for the Ciclonium cation.

With Pramiverin e.g. the hydrogen atom on the basic nitrogen atom can be replaced by a $C_1$–$C_6$ alkyl group; likewise then a still further $C_1$–$C_6$ alkyl group can be present to form the corresponding quaternary salts.

The combination of the invention for example in the following experimental models unexpectedly shows a potentiated spasmolytic action which compared to the spasmolytically active portion of the combination is increased above the additive amount.

Guinea pig small intestine in situ, carbon transport model on the guinea pig, gall bladder model on the mouse, rat bladder in situ (Postius, S. I. Szelenyi, J. Pharmacol, Methods 9, pages 53–61 (1983), rat uterus in situ (relying on the method of Postius), rat uterus in vitro (De Jalon, Bayo, DeJalon=Farmacoteraps, act. Volume 3, page 313 (1945); Pharmacological Experiments on isolated Preparations 2nd edition. E+S Livingstone Edinburgh and London 1970 (pages 92-93).

For example on the guines pig small intestine in situ (see Table 1 below) at a dosage of 100 mg/kg intraduodenally of butylscopolammonium bromide and 30 mg/kg intraduodenally of Flupirtin the spasmolytic activity of the butylscopolammonium bromide is increased about a factor of 2. In contrast the butylscopolammonium bromide alone upon intraduodenal dispensation shows no dosage dependent spasmolytic activity. It is only through the combination with Flupirtin that a considerable increase in activity is attained, in which case this activity is dosage dependent.

Flupirtin applied alone intraduodenally on the guinea pig small intestine has no spasmolytic activity. It is the more surprising that for example giving increasing amounts of Flupirtin and a constant amount (100 mg/kg intraduodenally) of butylscopolammonium bromide the Flupirtin likewise shows a clear spasmolytic effect which for the Flupirtin in the combination results in an $ED_{50}$ of 19.5 mg/kg (calculation of $ED_{50}$ by means of linear regression).

In the carbon transport model on the guinea pig (see Table 2 below) for example at a dosage of 100 mg/kg per os of butylscopolammonium bromide and 40 mg/kg per os of Flupirtin hydrochloride in comparison to the experiment with 40 mg/kg per os of Flupirtin dispensed alone, the carbon transport is retarded by a factor of 2, based on the effectiveness of Flupirtin alone. The peroral $LD_{50}$ of butylscopolammonium bromide dispensed alone for example on the above model, is 132 mg/kg.

The peroral $ED_{50}$ of the spasmolytic component of Flupirtin in the combination for example is 92 mg/kg. In contrast for example a peroral $ED_{50}$ of Flupirtin dispensed alone in a dosage range of 20 to 80 mg/kg cannot be calculated because of the weaker and non-dosage dependent effect.

It is surprisingly that the analgetic side component of the spasmolytic is increased as well as the analgetic main effect of Flupirtin (Acetic Acid-Writhing-Test on the mouse). For example, the analgetic effect of Flupirtin in the Acetic-Acid-Writhing-Test (see Table 3a) in the combination with butylscopolammonium bromide is increased overadditively by a factor of 30. Thereby butylscopolammonium bromide is held constant at 1 mg/kg per os and Flupirtin delivered in the dosages 0.1; 0.5; 1; 2; and 4 mg/kg.

For example the analgetic effect of butylscopolammonium bromide in the Acetic Acid-Writhing-Test in the combination with Flupirtin is increased about a fraction of 21. Thereby flupirtin is held constant at 10 mg/kg per os and butylscopolammonium bromide is delivered in the dosages 0.01; 0.05; 0.1; 0.5 mg/kg. The Flupirtin thereby was investigated as the maleate, gluconate or hydrochloride.

The same is true for example for the combination Flupirtin-Ciclonium bromide according to Table 3b.

For example the dose which is already analgetically effective in the Acetic Acid-Writhing-Test on the mouse is the combination of 0.1 mg/kg per os of Flupirtin and 1.0 mg/kg per os of butylscopolammonium bromide.

For example the dose which is already spasmolytically effective on the guinea pig small instestine in situ is the combination of 30 mg/kg intraduodenally of Flupirtin and 50 mg/kg intraduodenally of butylscopolammonium bromide or 20 mg/kg intraduodenally of Flupirtin and 100 mg/kg intraduodenally of butylscopolammonium bromide.

For example, the dose which is already spasmolytically effective on the carbon transport model on the guinea pig is the combination of 20 mg/kg per os of Flupirtin and 100 mg/kg per os of butylscopolammonium bromide.

For example the dose which is already spamolytically effective on the gall bladder model on the mouse (see Table 4) is the combination of 3 mg/kg per os of Flupirtin and 100 mg/kg per os of butylscopolammonium bromide.

For example the dosage range of the combination for effectiveness in the Writhing-Test (mouse) is:
0.1-44 mg/kg of Flupirtin and 0.01-2 mg/kg of butylscopolammonium bromide.

In the Acetic-Acid-Writhing Test on the mouse for example the weight ratio of Flupirtin to the spasmolytic butylscopolammonium bromide is as follows:
1 part by weight Flupirtin to 10 parts by weight spasmolytic, preferably 1 part by weight Flupirtin to 1 part by weight spasmolytic, especially 1 part by weight Flupirtin to 0.001 to 0.05 part by weight spasmolytic.

For example the synergistic action on the same animal model is especially in the following range of weight ratios of Flupirtin and spasmolytic:
Flupirtin: butylscopolammonium bromide from 10:0.0 to 0.1:1.

The total dosage for the combination in the animal experiments for example is between 1.1 mg/kg and 200 mg/kg, preferably between 1.1 and 130 mg/kg especially between 1.1 and 100 mg/kg per os.

For example there is obtained a 50% inhibition of the writhing syndrome (=inhibition of pain) calculated for the synergistic analgetic effect of Flupirtin and spasmolytic on the Writhing-Test on the mouse: 1.4 mg/kg per os of Flupirtin and 1 mg/kg per os of butylscopolammonium bromide or 10 mg/kg per os of Flupirtin and 0.07 mg/kg per os of butylscopolammonium bromide. For example there is obtained a 50% inhibition of the acetylcholine spasm calculated for the spasmolytic effect of Flupirtin and spasmolytic on the guinea pig small intestine in situ at 30 mg/kg per os of Flupirtin and 49 mg/kg per os of butylscopolammonium bromide or 100 mg/kg per os of butylscopolammonium bromide and 19.5 mg/kg per os Flupirtin.

There are the following indications for the combination of the invention: acute and chronic spastic pain conditions, gall colic, spasms in the gall duct, gall bladder and gall duct dyskinesia, kidney colic, pains in the area of the urinary passages, the bladder and the urethra, spastic pains in the area of the gastrointestinal tract, dysmenorrhea, navel colic, post-operative pain conditions, spastic pains before, during and after diagnostic procedures and therapeutic measures, especially in the area of the kidney pelvis and the urinary passages, the gall bladder and the bile ducts as well as the gastrointestinal tract including the colon and the rectum.

Contraindications: narrow angle glaucoma, prostate adenoma with residual formation of urine, mechanical stenosis in the area of the gastrointestinal canal, tachyarrhythemia, megacolon.

According to the invention there is dispensed a combination of Flupirtin and the spasmolytic in a daily dosage of 10 to 900 mg, for example 10 to 600 mg, preferably 50 to 600 mg, for example 50 to 400 mg, especially 100 to 400 mg (for example 100 to 300 mg) of Flupirtin and 0.1 to 150 mg, preferably 0.1 to 100 mg, especially 0.5 to 50 mg of the spasmolytic (based on the basic cation).

The daily dose can be employed in the form of a single dispensation of the total amount or in the form of 1 to 6, especially 1 to 4 partial doses per day. Generally there is preferred a dispensation 1 to 3-4 times. For example the preferred dosage for the combination of Flupirtin and butylscopolammonium bromide is 100-600 mg (for example 100-500 mg) Flupirtin and about 10-50 mg butylscopolammonium bromide 1 time daily. Especially for the mentioned example this dosage is about 100-400 mg Flupirtin and about 10-30 mg butylscopolammonium bromide one time daily. With several applications daily the mentioned dosages are employed in corresponding partial amounts.

For the rest there is valid for the spasmolytic components what is known in this regard in the literature and the proposed daily dosages (see for example Table 5).

Preferably the medicine is dispensed orally.

Flupirtin and each spasmolytic can be used in each case as separate formulations or together in a galenical formulation. According to a preferred illustration of the invention the medicine can be formulated in the form of an individual dosage (that is in the form of a mixture) for peroral, parenteral (intravenous, intramuscular, subcutaneous), rectal dispensation, for example in the form of tablets, capsules, pills, dragees, suppositories, a solution, suspension or emulsion, whereby the active materials are combined with corresponding adjuvants and carriers. A formulation with controlled release is also possible with the peroral form of the medicine.

The compounds serving as active materials, that is the Flupirtin and the spasmolytic employed in each case are present in a dosage unit for example in a weight ratio which contains per part by weight Flupirtin, 0.05 to 150, preferably 0.1 to 100, especially 0.1 to 10 parts by weight of the spasmolytic. Hereby the parts by weight of spasmolytic in each case refer to the fundamental basic cation of the spasmolytic respectively to the free base of the spasmolytic. In using the salts of the spasmolytics naturally because of the additional anions there must be calculated in each case correspondingly higher amounts by weight.

For example for the combination with the spasmolytics there is formulated 1 to 10 mg butylscopolammonium bromide and 1 to 200 mg (for example 1 to 150 mg) Flupirtin preferably 2 to 9 mg butylscopolammonium bromide and 10 to 150 mg (for example 10 to 100 mg) Flupirtin, especially 3 to 7 mg butylscopolammonium bromide and 15 to 100 mg (for example 15 to 60 mg) Flupirtin.

This is true only for homogeneous mixtures of spasmolytic and Flupirtin in the above-stated weight ratios. These data are not automatically true with capsules and two layer tablets.

The amounts by weight of spasmolytic below refer in each case to the base or the base cation. The same is true for the Flupirtin.

The individual dosages of the combination according to the invention can be:

(a) with peroral medicines which contain a spasmolytic of the group of butylscopoammonium salts:

50 to 300, preferably 100 to 200, especially 100 to 150 mg Flupirtin and 1 to 40, (for example 2 to 35 mg), preferably 2 to 30 (for example 4 to 20), especially 5 to 15 (for example 10 mg) spasmolytic. This dosage can be dispensed for example 1 to 4, preferably 1 to 3, especially 1 to 2 times daily.

with peroral medicines which contain a spasmolytic of the group of Trospium salts:

50 to 300, preferably 100 to 200 mg, especially 100 to 150 mg Flupirtin and 1 to 10, preferably 2 to 8 mg, especially 2 to 4 mg spasmolytic. This dosage can be dispensed for example 1 to 4, preferably 1 to 3, especially 1 to 2 times daily.

with peroral medicines which contain a spasmolytic of the group of Pramiverin salts:

50 to 300, preferably 100 to 200, especially 100 to 150 mg Flupirtin and 1 to 10, preferably 1 to 6, especially 2 to 4 mg spasmolytic. This dosage can be dispensed for example 1 to 4, preferably 1 to 3, especially 1 to 2 times daily.

with peroral medicines contain a spasmolytic of the group of Fenpiverin salts:

50 to 300, preferably 100 to 200, especially 100 to 150 mg Flupirtin and 0.01 to 1.0, preferably 0.05 to 0.6, especially 0.1 mg spasmolytic. This dosage can be dispensed for example 1 to 4, preferably 1 to 3, especially 1 to 2 times daily.

with peroral medicines which contain a spasmolytic of the group of Ciclonium salts:

50 to 300, preferably 100 to 200, especially 100 to 150 mg Flupirtin and 2 to 80, preferably 4 to 40, especially 10 to 20 mg of spasmolytic. This dosage can be dispensed for example 1 to 4, preferably 1 to 3, especially 1 to 2 times daily.

(b) with parenteral medicines which contain a spasmolytic of the group butylscopolammonium salts:

50 to 200, preferably 75 to 150, especially 100 mg Flupirtin and 0.01 to 100, preferably 0.05 to 50, especially 0.1 to 5 mg spasmolytic. This dosage can be dispensed for example 1 to 6, preferably 1 to 4, especially 1 to 2 times daily.

with parenteral medicines which contain a spasmolytic of the group of Trospium salts:

50 to 200, preferably 75 to 150, especially 100 mg Flupirtin and 0.01 to 1.0, preferably 0.1 to 0.6, especially 0.2 to 0.4 mg spasmolytic. This dosage can be dispensed for example 1 to 6, preferably 1 to 4, especially 1 to 2 times daily.

with parenteral medicines which contain a spasmolytic of the group of Pramiverin salts and Fenpiverinium salts:

50 to 200, preferably 75 to 150, especially 100 mg Flupirtin and 0.5 to 10 mg, preferably 1 to 6, especially 2 to 4 mg spasmolytic. This dosage can be dispensed for example 1 to 6, preferably 1 to 4, especially 1 to 2 times daily.

with parenteral medicines which contain a spasmolytic of the group of Ciclonium salts:

50 to 200, preferably 75 to 150, especially 100 mg Flupirtin and preferably 2 to 50, especially 4 to 25 mg spasmolytic. This dosage can be dispensed 1 to 4, preferably 1 to 3, especially 1 to 2 times daily.

(c) with rectal medicines which contain a spasmolytic of the group of butylscopolammonium salts:

75 to 450, preferably 75 to 300, especially 100 to 200 mg Flupirtin and 1 to 40, preferably 2 to 30, especially 5 to 15 (for example 10 mg) spasmolytic. This dosage can be dispensed 1 to 4, preferably 1 to 3, especially 1 to 2 times daily.

with rectal medicines which contain a spasmolytic of the group or Pramiverin salts:

75 to 450, preferably 75 to 300, especially 100 to 200 mg Flupirtin and 1 to 20, preferably 2 to 10, especially 4 to 8 mg spasmolytic. This dosage can be dispensed 1 to 4, preferably 1 to 3, especially 1 to 2 times daily.

with rectal medicines which contain a spasmolytic of the group of Fenpiverin salts:

75 to 450, preferably 75 to 300, especially 100 to 200 mg Flupirtin and 0.01 to 1 preferably 0.01 to 0.8 mg, especially 0.1 to 0.2 mg spasmolytic. This dosage can be dispensed 1 to 4, preferably 1 to 3, especially 1 to 2 times daily.

with rectal medicines which contain as spasmolytic of the group of Ciclonium salts:

75 to 450, preferably 75 to 300, especially 100 to 300 mg Flupirtin and 1 to 100, preferably 2 to 60 mg, especially 5 to 40 (for example 10 to 20 mg) spasmolytic. This dosage can be dispensed 1 to 4, preferably 1 to 3, especially 1 to 2 times daily.

The acute toxicity of the combinations of the invention in the mouse (expressed by the $LD_{50}$ mg/kg; method of Litchfield and Wilcoxon, J. Pharmacol. Exper. Ther., Volume 95: 99, 1949) for example for the combination with Flupirtin and butylscopolammonium bromide (1:1) in oral application is for example 618 mg/kg respectively above 613 mg/kg body weight. For example the $LD_{50}$ of Flupirtin alone per os on the mouse: 552 mg/kg.

For example the preferred dosage for the combination of Flupirtin and butylscopolammonium bromide is 100 mg to 600 mg (for example 100 to 500 mg) Flupirtin and 10 to 50 mg butylscopolammonium bromide. Especially for the combination of Flupirtin and butylscopolammonium bromide this dosage is about 100 to 400 mg Flupirtin and about 10 to 30 mg butylscopolammonium bromide. This dosage unit can be dispensed for example 1 to 6, preferably 2 to 4, especially 2 to 3 times.

For example the preferred dosage unit for the combination of Flupirtin and Pramiverine HCl is 100 mg to 600 mg (for example 100 to 500 mg) Flupirtin and 1 to 12 mg Pramiverin HCl. Especially for the combination of Flupirtin and Pramiverin.HCl this dosage is about 100 to 400 mg Flupirtin and about 2 to 4 Pramiverin HCl.

For example the preferred dosage unit for the combination of Flupirtin and Trospium chloride is 100 to 600 mg (for example 100 to 500 mg) Flupirtin and 0.2 to 12 mg Trospium chloride. Especially for the combination of Flupirtin and Trospium chloride this dosage unit is 100 to 400 mg Flupirtin and 0.2 to 5 mg Trospium chloride. This dosage unit for example can be dispensed 1 to 6, preferably 1 to 4, especially 2 to 3 times.

For example the preferred dosage unit for the combination of Flupirtin and Fenpiverinium bromide is 100 to 600 mg (for example 100 to 500 mg) Flupirtin and 0.05 to 0.8 mg Fenpiverinium bromide. Especially for the combination of Flupirtin and Fenpiverinium bromide this dosage unit is 100 to 400 mg Flupirtin and 0.1 to 0.6 mg Fenpiverinium bromide. This dosage can be dispensed 1 to 6, preferably 1 to 4, especially 2 to 3 times.

For example the preferred dosage unit for the combination of Flupirtin and Ciclonium bromide is 100 mg to 600 mg (for example 100 to 500 mg) Flupirtin and 10 to 60 mg Ciclonium bromide. Especially for the combination of Flupirtin and Ciclonium bromide this dosage unit is 100 to 400 mg Flupirtin and 20 to 40 mg Ciclonium bromide. This dosage can be dispensed 1 to 6, preferably 1 to 4, especially 2 to 3 times.

It goes without saying that there can also be produced galenic preparations which contain the above-stated dosage units 2 to for example 6 times. Thus for example tablets or capsules of the combination of the invention can be produced which contain 25–900 mg of the Flupirtin component (with dispensation in the form of granulates, pellets, or powders (packed in sachets) for example 25–4000 mg of Flupirtin).

The combination according to the invention is suitable for the production of pharmaceutical compositions and preparations of pharmaceutical compositions or medicaments contain, as active principle Flupirtin in admixture with other pharmacologically or pharmaceutically active substances. The medicaments may be prepared in known manner with the usual pharmaceutical adjuvants, carriers, and diluents.

As carriers and adjuvants, for example, are those recommended in the following literature as adjuvants for pharmacy, cosmetic, and related fields such as Ullmann's Encyklopadie der technischen Chemie, Volume 4 (1953), pages 1–39, Journal of Pharmaceutical Sciences 52 (1963), pages 918 et seq; H. V. Czetsch-Lindenwald, Hilfsstole für Pharmazie und angrenzende Gebiete; Pharm. Ind. 2 (1961), pages 72 et seq; Dr. H. P. Fiedler, Lexikin der Hilffsstoffe für Pharmazie, Kosmetik und angrenzende Gebiete, 2nd edition, Editio Cantor Aulendorf i. Württ (1981).

Examples of such materials include gelatin, natural sugars such as sucrose or lactose, lecithin, pectin, starch (for example, cornstarch, cyclodextrin and cyclohextrin derivatives as well as starch derivatives), polyvinyl-pyrrolidone, gelatins, cellulose derivatives (for example cellulose ethers) in which the cellulose hydroxy groups are partially etherified with lower saturated aliphatic alcohols and/or lower saturated aliphatic alcohols and/or lower saturated aliphatic alcohols and/or lower saturated hydroxy-alcohols (for example methyl cellulose, hydroxypropylmethyl cellulose), stearates, e.g. methyl stearate and glyceryl stearate, magnesium and calcium salts of fatty acids with 2 to 22 (especially 10 to 18) carbon atoms, especially saturated acids (for example, calcium stearate, calcium laurate, magnesium oleate, calcium palmitate, calcium behenate and magnesium stearate), emulsifiers, oils, and fats (castor oil, olive oil, sesame oil, cottonseed oil, corn oil, wheat germ oil, sunflower seed oil, cod-liver oil), mono-di- and triglycerides of saturated fatty acids $C_{12}H_{24}O_2$ to $C_{18}H_{38}O_2$ and their mixtures (e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, penterythritol, ethyl alcohol, diethylene glycol, triethyl glycol, propylene glycol, dipropylene glycol, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, penterylthritol, sorbitol, mannitol, ethyl alcohol, butyl alcohol, octadecyl alcohol, etc. e.g. glyceryl stearate, glyceryl palmitate, glycol distearate, glycol dilaurate, glycol diacetate, monoacetin, triacetin, glyceryl oleate, ethylene glycol sterate, such esters of polyvalent alcohols can in a given case also be etherified, benzyl benzoate, dioxolane, glycerine formal tetrahydrofurfuryl alcohol, polyglycol ethers with 1 to 12 carbon atoms alcohol, dimethyl actamide, lactamide, lactates, e.g. ethyl lactate, ethyl carbonate, silicones (especially middle viscosity dimethyl polysiloxane), calcium carbonate, sodium carbonate, sodium phosphate.

As further adjuvants there can be used materials which cause disintegration (so-called disintegrants) such as: cross-linked polyvinyl pyrrolidone, sodium carboxymethyl-starch, sodium carboxymethyl cellulose or microcrystalline cellulose. Likewise there can be used coating materials such as for example: polyacrylic acid esters, cellulose ethers and the like.

For the production of solutions there can be used water or physiologically compatible organic solvents, as for example, ethanol, 1,2-propylene glycol, polyglycols, e.g. diethylene glycol, triethylene glycol, and dipropylene glycol and their derivatives, dimethyl sulfoxide, fatty alcohols, e.g. stearyl alcohol, acetyl alcohol, lauryl alcohol, and oleyl alcohol, triglycerides, e.g. glyceryl oleate, glyceryl stearate, glyceryl palmitate, and glyceryl acetate, partial esters of glycerine, e.g. monoacetin, diacetin, glyceryl monostearate, glyceryl distearate, glyceryl monopalmitate, paraffins and the like.

For injectable solutions or suspensions there can be used non-toxic parenteral compatible diluents or solvents such as for example, water, 1,3-butanediol, ethanol, 1,2-propylene glycol, polyglycols mixed with water, Ringer's solution, isotonic salt solution or even hardened oils including synthetic mono or diglycerides or fatty acids such as oleic acid.

In the production of the preparation there can be used known and customary solution aids or emulsifiers. As solution aids and emulsifiers there can be used, for example, polyvinyl pyrrolidone, sorbitan fatty acids esters such as sorbitan trioleate, phosphatides such as lecithin, gum acacia, gum tragacanth, polyoxyethylated sorbitan monooleate, polyoxyethylated fats, polyoxyethylated oletriglycerides, linolized oleotriglyerides, polyethylene oxide-condensation products of fatty alcohols, alkylphenols or fatty acids or even 1-methyl-3-(2-hydroxyethyl)-imidazolidone-2. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glycerides).

Examples of oletriglycerides are olive oil, peanut oil, castor oil, sesame oil, cottonseed oil, corn oil (see also Dr. H. P. Fielder, supra pages 338–345).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value.

As antioxidants there can be used for example sodium bisulfite, ascorbic acid, gallic acid, butyl hydroxyanisole, nordihydroguaiaretic acid, tocopherols, as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmaceutical and galenical treatment of the compounds of the invention takes place according to the usual standard methods. For example, the active material or materials and assistants or carriers are well mixed by stirring or homogenization (for example, by means of a colloid mill or ball mill or other customary mixing apparatus) wherein the operation is generally carried out at temperatures between 20° C. and 80° C., preferably 20° C. to 50° C., especially at room temperature. For the rest reference is made to the following standard work:

Sucker, Fuchs, Speiser, Pharmazeutische Technologie, Thieme-Verlag, Stuttgart, 1978 Voigt, Lehrbuch der Pharmazeutischen. Technologie, 3rd Edition, Verlag Chemie, Weinheim and New York, 1979; List, Arzneiformenlehre, Wissenschaftliche Verlagsgesellschaft mbH, Stuttgart, 1976, Description of the Cited Pharmacological Test Models Carbon Transport Model (Influence on the Gastrointestinal Passage (Guinea Pigs)

Relying on Komlus and Petöcz (and modifications) (1970) Arzneim Forsch. Volume 20, pages 1338–1357 guinea pigs received 30 minutes after being given the substance a 10% carbon suspension in demineralized water in a volume of 1 ml/animal dispensed with the stomach probe. 0.5 hours later the animals were killed and starting from the stomach there was measured on one animal the entire length of intestine, on the others the length of the stretch blackened by the carbon. The stretch changed by the carbon was calculated in percent of the entire length in order to compensate for the different intestinal lengths of the individual animals in the evaluation of the effect of the substance. The effect on the gastro-intestinal passage is given from the comparison between the control and the animals (average value) treated with the substances. Ascertaining the $ED_{50}$ (dosage in mg/kg at which there is 50% retardation of the carbon transport) is by means of linear regression.

Retardation of carbon transport signifies spasmolytic effect. The greater this retardation the greater also is the spasmolytic effect.

Acetic Acid-Test (Writhing Test) on the Mouse

In the acetic acid test according to Koster et al (Fed. Proc., Volume 18 (1959), page 412) the irritating pain was caused by an intraperitoneal injection of 1% acetic acid. The pain reaction is expressed as a characteristic stretching of the animals ("writhing symdrome") which persists in irregular time intervals for a long period of time after the injection of the acetic acid. The dosage dependent suppression of the frequency of the stretching motion compared to an untreated control group is expressed in percent as analgetic effect. The evaluation is carried out by determination of the $ED_{50}$ (Method of Linear Regression). The $ED_{50}$ is the dosage in mg/kg present at which mathematically a 50% suppression of the 'writhing syndrome' is present.

The acetic acid test is marked by the fact that not only is there detectable the effect of strong, central acting analgetics but also preponderantly peripherally acting analgetics-antipyretics and antiphlogistically active pharmaceuticals such as phenyl butazone, Indometacin and others. Therewith the effect in this procedure refers to a peripheral component of the analgesic.

Spasmolytic on the Guinea Pig Small Intestine

A balloon catheter was introduced into the ileum of guinea pigs narcotized with urethane (1.8 g/kg subcutaneously) after tracheotomy (tying up a tracheal channel to make breathing easier) and the catheter filled with air.

Rhythmic contractions were carried out by the intestine, the so-called peristaltics (dependent upon filling), through which a pressure is exerted on the rubber balloon. The pressure exterted and their changes were recorded on a linear recorder via a pressure recorder connected to the balloon catheter and a carrier frequency bridge (TF of Hellige Co.). On one there can be measured the spontaneous peristaltics, on the other the spasms released by superfusion of spasmolytics (acetylcholine iodide, barium chloride or carbachol). By previously giving the spasmolytics intravenously or intraduodenally the height of the spasms released is retarded and can be determined in percent spasmolysis compared to a starting value. There is given as spasmolytic effect or spasmolysis how great a percent of spasm is liberated by the spasmogen (e.g. acetylcholine iodide) compared to the value which originates from the spasmogen (on the same animal).

Ascertaining the $ED_{50}$ (dosage in mg/kg present at 50% spasmolysis) is by means of linear regression.

Gall Bladder Model on the Mouse

The experiment is carried out relying on the methods of Valsecchi and Toson, J. Pharmacol. Methods Volume 7, pages 193 et. seq. (1982).

The principle of this method is the gravimetric measurement of the gall bladder of the mouse.

The gall bladder was stimulated through dispensation of egg yolk for delivery of bile. This delivery was carried out through natural spasms of the gall bladder. By previously dispensing a spasmolytically acting test material these spasms of the gall bladder were retarded and therewith likewise the delivery of bile.

Thus the heavier the gall bladder is after dispensing the egg yolk the less bile it has delivered. The weight of the gall bladder in this test therefore is a measure of the spasmolytic effect of a material.

The materials to be tested were dispensed for the animals perorally in 1% Methocel (methyl cellulose) suspension. 10 animals were employed per dosage. The control animals received Methocel in the corresponding amount.

Application volume: 30 ml/kg.

Because of the evaluation 2 control groups must be present.

15 minutes after being given the material the animals of control group No. 1 received 1 ml NaCl 0.9%/animal perorally, the other control group No. 2 as well as the material groups received 1 ml of egg yolk suspension 30%/animal orally.

The egg yolk suspension consisted of 3 parts by weight egg yolk in 7 parts by weight NaCl 0.9%. For this reason control group No. 1 also received 1 ml NaCl 0.9%.

30 minutes after giving the materials the animals were killed with ether. The gall bladder was prepared and weighed.

Statistic:

The evaluation was carried out according to the formula:

$$[(A-B)/(C-B)] \times 100 = \% \text{ Activity}$$

wherein A is the arithmetic average value of each substance group, B is the egg yolk control and C is the Methocel control (control group No. 1).

Literature:

B. Valsecchi and G. Toson: Journal of Pharmacological Methods 7, pages 193–195 (1982)

TABLE 1

Effect on the Guinea Pig Small Intestine In Situ
Spasmogen: Acetylcholine iodide $1 \times 10^{-4}$ g/ml

| Active Materials Combination | Dosage (mg/kg) Intraduodenally | Number of Animals | % Spasmolytic Effect (negative value) $ED_{50}$ in mg/kg 30 Minutes after Dispensation | |
| --- | --- | --- | --- | --- |
| Flupirtin | 10.0 | 6 | no spasmolytic | |
| (Maleate) | 30.0 | 6 | Effect | |
| alone | 50.0 | 4 | | |
| | | | | This retardation is not dosage dependent and |
| Butylscopol- | 50.0 | 6 | −13.1% | therefore an |
| ammonium bromide | 100.0 | 6 | −37.9% | $ED_{50}$ cannot be |
| alone | 200.0 | 6 | −35.0% | determined |
| | Butylscopol-ammonium bromide | | Butylscopolammonium bromide | |
| Flupirtin (maleate, 30,0 mg/kg) + Butylscopolammonium bromide | 10,0 | 6 | −8,8 | |
| | | | ED 50 | |
| | 50.0 | 6 | −45.1% 48.6 mg/kg | |
| | 100.0 | 6 | −73.5% | |
| 100.0 mg/kg Butylscopolammonium bromide + | Flupirtin (maleate) | | from Flupirtin (maleate) | |
| Flupirtin | 10.0 | 6 | −12.3% | |
| (maleate) | 20.0 | 6 | −52.5% 19.48 mg/kg | |

TABLE 1-continued

Effect on the Guinea Pig Small Intestine In Situ
Spasmogen: Acetylcholine iodide $1 \times 10^{-4}$ g/ml

| Active Materials Combination | Dosage (mg/kg) Intraduodenally | Number of Animals | % Spasmolytic Effect (negative value) $ED_{50}$ in mg/kg 30 Minutes after Dispensation |
|---|---|---|---|
| | 30.0 | 6 | −73.5% |

Method: Calculation of the $ED_{50}$ by means of linear regression

TABLE 2

Action in the Carbon Transport Model with Guinea Pigs
6 animals were used in each dosage group

| Active material Combination | Dosage (mg/kg) Peroral | Spasmolytic Effect Retardation in % (negative value) | $ED_{50}$* in mg/kg |
|---|---|---|---|
| Flupirtin (HCl) alone | Flupirtin (HCl) 20.0 | −11.73% | not dosage dependent only being weak Effect of Butylscopolammonium bromide |
| | 40.0 | −21.55% | |
| | 80.0 | −18.70% | |
| | Butylscopolammonium bromide | | |
| Butylscopolammonium bromide alone | 30.0 | −8.16% | |
| | 100.0 | −58.39% | 131.6 |
| | 300.0 | −61.62% | |
| Butylscopolammonium bromide (100 mg/kg) + Flupirtin (HCl) | Flupirtin (HCl) | | of Flupirtin (HCl) |
| | 1.0 | −1.3% | |
| | 10.0 | +5.1% | |
| | 20.0 | −35.2% | 91.8 |
| | 40.0 | −45.0 | |
| | 80.0 | −50.3% | |
| | 100.0 | −54.3% | |

*Calculation of the $ED_{50}$ by means of linear regression

TABLE 3a

Analgetic Effect In the Writhing-Test (NMRI-Mouse)
(Koster et al: Fed. Proc. 18, 412 (1959))

| Active Material Combination | Dosage (mg/kg) per os | Effect in % Average of 10 mice | $ED_{50}$ after 30 minutes: in mg/kg |
|---|---|---|---|
| Flupirtin (Gluconate) alone | 0.56 | 19.2% | of Flupirtin (Gluconate) |
| | 1.12 | 28.0% | |
| | 2.24 | 37.6% | |
| | 4.47 | 46.4% | 43.9% |
| | 8.93 | 38.4% | |
| | 17.85 | 22.4% | |
| | 35.7 | 61.6% | |
| Flupirtin (maleate) alone | 20.0 | 12.0% | of Flupirtin (maleate) 44.7 |
| | 40.0 | 54.0% | |
| | 80.0 | 70.0% | |
| Butylscopolammonium bromide alone | 0.5 | 22.4% | Butylscopolammonium bromide 1.5 |
| | 1.0 | 48.4% | |
| | 2.0 | 64.6% | |
| | 4.0 | 59.0% | |
| 10 mg/kg Flupirtin (HCl) + Butylscopoammonium bromide | Butylscopolammoniumbromide | | of Butylscopolammonium bromide |
| | 0.01 | 25.2% | |
| | 0.05 | 48.3% | 0.07 |
| | 0.1 | 60.1% | |
| | 0.5 | 68.5% | |
| 1.0 mg/kg Butylscopolammonium bromide + Flupirtin (HCl) | Flupirtin (HCl) | | of Flupirtin (HCl) |
| | 0.1 | 30.8% | |
| | 0.5 | 36.8% | |
| | 1.0 | 53.4% | 1.4 |
| | 2.0 | 52.6% | |
| | 4.0 | 56.4% | |

Method 1: Calculation of the $ED_{50}$ by means of linear regression

TABLE 3b

Analgetic Effect on the Writhing-Test (NMRI-Mouse)
Koster et al, Fed. Proc. 18, 412 (1959)

| Active Material Combination | Dosage (mg/kg) per os | Effect in % Average of 10 mice | $ED_{50}$ after 30 minutes in mg/kg |
|---|---|---|---|
| Ciclonium bromide, alone | 0.01 | 18.5 | of Ciclonium bromide alone |
|  | 0.1 | 46.3 |  |
|  | 0.5 | 53.1 | 0.26 |
| Ciclonium bromide + 2.24 mg/kg Flupirtin (HCl) | Ciclonium bromide 0.001 | 33.1 | Ciclonium bromide 0.01 |
|  | 0.01 | 53.1 |  |
|  | 0.05 | 58.1 |  |

Determination of the $ED_{50}$ by means of linear regression

TABLE 4

Effect on the Gall Bladder Model on the NMRI-Mouse
(valsecchi and Tonson, J. Pharmacol methods 7, 193-195, 1982)
In each dosage group 10 animals were used

| Active material, Combination | Dosage mg/kg peroral | Spasmolytic Effect in % | $ED_{50}^*$ in mg/kg |
|---|---|---|---|
|  | Flupirtin (HCl) |  | Flupirtin (HCl) |
| Flupirtin (HCl) alone | 1.0 | 30.06% | 2.4 |
|  | 3.0 | 64.36% |  |
|  | 10.0 | 69.25% |  |
| Butylscopol-ammonium bromide alone | | | of Butylscopolammonium bromide |
|  | 3.0 | 4.6% |  |
|  | 10.0 | 19.1 |  |
|  | 30.0 | 20.7% | 116.6 |
|  | 100.0 | 35.9% |  |
|  | 300.0 | 76.6% |  |
| 3 mg/kg Flupirtin (HCl) + Butylscopol-ammonium bromide | Butylscopol-ammonium bromide | | of Butylscopol-ammonium bromide |
|  | 1.0 | 2.70% |  |
|  | 10.0 | 38.30% | 100.2 |
|  | 30.0 | 24.10% |  |
|  | 100.0 | 54.80% |  |
| Butylscopol-ammonium bromide (100 mg/kg) + Flupirtin (HCl) | Flupirtin (HCl) | | of Flupirtin (HCl) |
|  | 1.0 | 23.7% |  |
|  | 3.0 | 31.9% | 3.7 |
|  | 10.0 | 65.5% |  |
|  | 30.0 | 125.6% |  |

*Calculation of the $ED_{50}$ by means of linear regression

TABLE 5

Doses for the Spasmolytic Components

| Material | Daily Dosage | Individual Doses | Daily Application Frequence |
|---|---|---|---|
| Butylscopol-ammonium bromide Dragees | 30–50 mg | 10 mg | 3–5 |
| Butylscopol-ammonium bromide Suppositories | 10–20 mg | 10 mg | 1–2 |
| Butylscopol-ammonium bromide Ampoule | 20 mg | 20 mg | 1 |
| Pramiverin Ampoule | 2.25–4.5 mg | 2.25 mg | 1–2 |
| Pramiverin Drops | 25 drops 3 × a day | 1 ml = 2 mg | 3–4 |
| Pramiverin Suppositories | 6–12 mg 3 × a day | 6 mg | 1–2 |
| Trospium chloride Ampoule | 0.2–0.4 mg | 2 ml = 0.2 mg | 1–2 |
| Trospiumchloride Suppositories | 1–5 mg | 1 mg | 1–5 |
| Trospiumchloride Tablets | 2–12 mg | 2 mg | 1–3 |
| Fenpiverinium-bromide Ampoule | 2–5 ml 0.05–0.1 mg | 5 ml = 0.1 mg | 1–2 |
| Fenpiverinium-bromide Tablets | 0.1–0.8 | 0.1 mg | 1–4 |
| Fenpiverinium-bromide Suppositories | 0.2–0.3 mg | 0.1 mg | 2–3 |
| Cicloniumbromide Ampoule | 12.5–25 mg | 1 ml = 5 mg | 1 |
| Cicloniumbromide Tablets | 20–60 mg | 10 mg | 2–3 |
| Cicloniumbromide Suppositories | 40–60 mg | 20 mg | 2–3 |

The composition can comprise, consist essentially of, or consist of the states materials and the process can comprise, consist essentially of or consist of the recited steps with such materials.

The composition can be used in human or veterinary medicine, e.g. to treat dogs, cats, cattle, sheep, and horses.

Unless otherwise indicated all parts and percentages are by weight.

DETAILED DESCRIPTION

EXAMPLE 1

Capsules Containing 40 mg Flupirtin Maleate and 5 mg Butylscopolammonium Bromide 80 grams of Flupirtin maleate were mixed with 10 grams of butylscopolammonium bromide and 160 grams of cellulose and subsequently granulated in the customary manner with a solution of 3 grams Kollidon VA64 (BASF) (Kollodian VA64 is a vinylpyrrolidone-vinyl acetate copolymer 60:40) in 115 ml of water. The dried granulate was passed through a sieve having a 0.8 mm mesh size and subsequently mixed with 4 grams of magnesium stearate and 1 gram of highly dispersed silica (Aerosil 200/Degussa) and 42 grams of modified starch (Starch 1500/Colorcon; which is free flowing and partially cold water soluble corn starch; this modification is carried out through purely physical procedures).

The mixture in each case in an amount of 150 mg was filled into hard gelatin capsules of size 3.

One capsule contains 40 mg Flupirtin maleate and 5mg butylscopolammonium bromide.

In an analogous manner there can be produced capsules containing 100 mg Flupirtin maleate and 10 mg N-Butylscopolammonium bromide.

EXAMPLE 2

Suppositories Containing 40 mg Flupirtin Maleate and 5 mg Butylscopolammonium Bromide 20 grams of Flupirtin maleate and 2.5 grams of butylscopolammonium bromide were suspended in 997.5 grams of molten hard fat. After homogenization the suspension was poured into 2.3 ml hollow cells in customary manner and cooled.

A suppository weighing 2.04 grams contains 40 mg of Flupirtin maleate and 5 mg of butylscopolammonium bromide.

In a similar manner suppositories containing 150 mg of Flupirtin maleate and 10 mg of butylscopolammonium bromide can be produced.

Hard fat is a mixture of mono-, di-, and triglycerides of saturated fatty acids from $C_{10}H_{20}O_2$ to $C_{18}H_{36}O_2$.

EXAMPLE 3

Capsules containing 40 mg Flupirtin Maleate and 0.1 mg Fenpiverinium Bromide 80 grams of Flupirtin maleate were mixed with 169.8 grams of cellulose and granulated in the usual manner with a solution of 0.2 grams of Fenpiverinium bromide and 3 grams of Kollidon VA64 (BASF) in 120 ml of water. The dried granulate was passed through a sieve having a mesh size of 0.8 mm and subsequently mixed with 4 grams of magnesium stearate, 1 gram of highly dispersed silica and 42 grams of modified starch (starch 1500/Colorcon).

The mixture was filled in each case in an amount of 150 mg into hard gelatin capsules of size 3.

One capsule contains 40 mg of flupirtin maleate and 0.1 mg of Fenpiverinium bromide.

EXAMPLE 4

Capsules Containing 40 mg Flupirtin Maleate and 2 mg Pramiverin HCl 80 grams of Flupirtin maleate were mixed with 166 grams of cellulose and the mixture granulated with a solution of 4 grams of Pramiverin HCl and 3 grams of Kollidon VA64 (BASF) in 115 ml of water in customary manner. The dried granulate was passed through an 0.8 mm mesh sieve and subsequently mixed with 4 grams of magnesium stearate, 1 gram of highly dispersed silica and 42 grams of modified starch (starch 1500/Colorcon).

The mixture in each case in an amount of 150 mg was filled into size 3 hard gelatin capsules.

One capsule contains 40 mg of Flupirtin maleate and 2 mg of Pramiverin HCl.

EXAMPLE 5

Suppositories Containing 40 mg Flupirtin Maleate and 6 mg Pramiverin HCl 20 grams of Flupirtin maleate and 3 grams of Pramiverin HCl were suspended in 997 grams of molten hard fat. After homogenization the suspension was poured into 2.3 ml hollow cells in customary manner and cooled.

A suppository weighing 2.04 grams contains 40 mg of Flupirtin maleate and 6 mg of Pramiverin HCl.

EXAMPLE 6

Tablets Containing 75 mg Flupirtin Maleate and 10 mg Ciclonium Bromide 300 grams of Flupirtin maleate were mixed with 40 grams of ciclonium bromide and the mixture granulated in the customary manner with a mucilage made of 20 grams of corn starch in 370 grams of water. After drying the granulate was passed through a sieve having a mesh size of 0.8 mm and subsequently mixed with 300 grams of microcrystalline cellulose, 52 grams of modified starch (starch 1500/Colorcon), 1 gram of highly dispersed silica (Aerosil 200/Degussa) and 7 grams of magnesium stearate. The mixture was pressed to tablets weighing 180 mg and having a diameter of 8 mm and a radius of curvature of 8 mm.

Subsequently the tablets in a give case, can be provided in the usual manner with a film coating.

One tablet contains 75 mg of Flupirtin maleate and 10 mg of Ciclonium bromide.

EXAMPLE 7

Suppositories Containing 75 mg Flupirtin Maleate and 10 mg Ciclonium Bromide 37.5 grams of Flupirtin maleate and 5 grams of Ciclonium bromide were suspended in 982.5 grams melted hard fat. (Hard fat is a mixture of mono-, di-, and triglycerides of saturated fatty acids of the formula $C_{10}H_{20}O_2$ to $C_{18}H_{36}O_2$, decanoic acid to stearic acid). After homogenization the suspension was poured into 2.3 ml hollow cells in customary manner and cooled.

A suppository weighing 2.05 grams contains 75 mg of Flupirtin maleate and 10 mg of Ciclonium bromide.

The entire disclosure of German priority application P No. 3506508.7 and P No. 3510348.5 is hereby incorporated by reference.

What is claimed is:

1. A medicine containing as the active material flupirtin and butylscopolammonium salt as a compound having both an anticholinergic acting spasmolytic effect and also an analgetic side effect, the flupirtin and butylscopolammonium salt being present in an amount effective to act synergistically as an analgetic and spasmolytic.

2. A material according to claim 1 wherein the flupirtin is present as flupirtin maleate and the butylscopolammonium salt is butylscopolammonium bromide.

3. A medicine according to claim 1 containing per part by weight of Flupirtin 0.05 to 150 parts by weight of spasmolytic.

4. A medicine according to claim 1 containing per part by weight of flupirtin 0.1 to 100 parts by weight of spasmolytic.

5. A medicine according to claim 1 containing 10 to 900 mg of Flupirtin and 0.3 to 100 mg of the spasmolytic.

6. A medicine according to claim 1 containing 10 to 600 mg of Flupirtin and 0.3 to 100 mg of the spasmolytic.

7. A medicine according to claim 1 containing 30 to 600 mg of Flupirtin and 3 to 60 mg of butylscopolamine.

8. A medicine according to claim 1 containing 30 to 400 mg of Flupirtin and 3 to 60 mg of butylscopolamine.

9. A process of providing analgetic and spasmolytic action to a mammal in need thereof comprising administering the medicine of claim 1 in an amount effective to act synergistically as an analgesic and spasmolytic.

10. A process according to 9 wherein there is administered 10 to 900 mg of flupirtin and 0.3 to 100 mg of the butylscopolammonium salt:

11. A process according to claim 10 wherein the flupirtin is administered as flupirtin maleate and the butylscopolammonium salt is butylscopolammonium bromide.

12. A process according to claim 9 wherein the flupirin is administered as flupirtin maleate and the butylscopolammonium salt is butylscopolammonium bromide.

* * * * *